United States Patent
Leveillard et al.

(10) Patent No.: US 10,857,239 B2
(45) Date of Patent: Dec. 8, 2020

(54) METHODS FOR THE TREATMENT AND DIAGNOSIS OF ALZHEIMER'S DISEASE AND TRAUMATIC BRAIN INJURIES

(71) Applicants: INSERM (Institut National de la Sante et de la Recherche Medicale), Paris (FR); Centre National de la Recherche Scientifique—CNRS, Paris (FR); Universite Pierre et Marie Curie (Paris 6), Paris (FR)

(72) Inventors: Thierry Leveillard, Paris (FR); Jose-Alain Sahel, Paris (FR); Hawa Camara, Paris (FR)

(73) Assignees: INSERM (INSTITUT NATIONAL DE LA SANTÉ ET DE LA RECHERCHE MÉDICALE), Paris (FR); CENTRE NATIONAL DE LA RECHERCHE SCIENTIFIQUE—CNRS, Paris (FR); UNIVERSITE PIERRE ET MARIE CURIE (PARIS 6), Paris (FR)

( * ) Notice: Subject to any disclaimer, the term of this patent is extended or adjusted under 35 U.S.C. 154(b) by 220 days.

(21) Appl. No.: 15/580,970

(22) PCT Filed: Jun. 10, 2016

(86) PCT No.: PCT/EP2016/063362
§ 371 (c)(1),
(2) Date: Dec. 8, 2017

(87) PCT Pub. No.: WO2016/198645
PCT Pub. Date: Dec. 15, 2016

(65) Prior Publication Data
US 2018/0179259 A1 Jun. 28, 2018

(30) Foreign Application Priority Data
Jun. 12, 2015 (EP) .................................... 15305913

(51) Int. Cl.
*A61K 48/00* (2006.01)
*G01N 33/68* (2006.01)
*C07K 14/47* (2006.01)
*A61P 25/28* (2006.01)
*C12Q 1/6883* (2018.01)

(52) U.S. Cl.
CPC .............. *A61K 48/00* (2013.01); *A61P 25/28* (2018.01); *C07K 14/4711* (2013.01); *C12Q 1/6883* (2013.01); *G01N 33/6896* (2013.01); *A01K 2227/105* (2013.01); *A01K 2267/0312* (2013.01); *C12Q 2600/118* (2013.01); *C12Q 2600/158* (2013.01); *G01N 2333/46* (2013.01); *G01N 2800/2821* (2013.01)

(58) Field of Classification Search
CPC ...... A61K 48/00; A61P 25/28; C07K 14/4711
See application file for complete search history.

(56) References Cited

FOREIGN PATENT DOCUMENTS

WO 2008/049058 A2 4/2008

OTHER PUBLICATIONS

Printout from en.wikipedia.org/wiki/Correlation_does_not_imply_causation. Printed Dec. 18, 2019. pp. 1-11 (Year: 2019).*
Congdon and Sigurdsson. Nat Rev Neurol 14(7):399-415, 2018; reprint pp. 1-37 (Year: 2018).*
Lee et al.; "hnRNP C promotes ApP translation by competing with FMRP for APP mRNA recruitment to P bodies"; Nature Structural and Molecular Biology, vol. 17, No. 6, Jun. 1, 2010, pp. 732-739.
Freibaum et al.; "Global analysis of TDP-43 interacting proteins reveals strong association with RNA splicing and translation machinery"; Journal of Proteome Research, vol. 9, No. 2, Feb. 5, 2010, pp. 1104-1120.
Kar et al.; "RNA Hilicase p68 (DDX5) Regulates tau Exon 10 Splicing by Modulating a Stem-Loop Structure at the 5' Splice Site"; Molecular and Cellular Biology, vol. 31, No. 9, May 1, 2011, pp. 1812-1821.
Jaillard et al.; "Nxn12 splicing results in dual functions in neuronal cell survival and maintenance of cell integrity"; Human Molecular Genetics, vol. 21, No. 10, 2012, pp. 2298-2311.

* cited by examiner

*Primary Examiner* — Marcia S Noble
(74) *Attorney, Agent, or Firm* — W&C IP

(57) ABSTRACT

The invention relates to the use of HNRNPC-expressing vectors for preventing and/or treating a tauopathy, such as Alzheimer's disease. The invention relates to methods for detecting a risk of developing a tauopathy such Alzheimer's disease in a patient, comprising the step of detecting the level of HNRNPC in a biological sample obtained from said patient.

Figure 1:
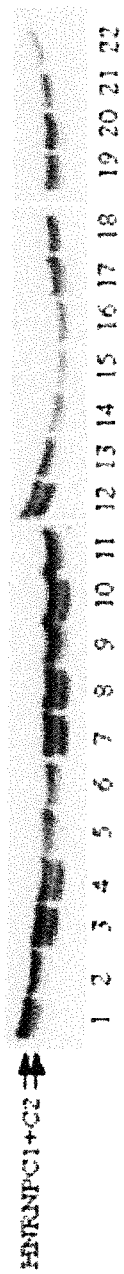

8 Claims, 2 Drawing Sheets
Specification includes a Sequence Listing.

METHODS FOR THE TREATMENT AND DIAGNOSIS OF ALZHEIMER'S DISEASE AND TRAUMATIC BRAIN INJURIES

FIELD OF THE INVENTION

The present invention relates to methods for the treatment and diagnosis of tauopathies such as Alzheimer's disease and traumatic brain injuries.

BACKGROUND OF THE INVENTION

Alzheimer's disease accounts for 60% to 70% of cases of dementia. It is a chronic neurodegenerative disease that usually starts slowly and gets worse over time. The most common early symptom is difficulty in remembering recent events (short-term memory loss). As the disease advances, symptoms can include: problems with language, disorientation (including easily getting lost), mood swings, loss of motivation, not managing self-care, and behavioural issues. As a person's condition declines, she or he often withdraws from family and society. Gradually, bodily functions are lost, ultimately leading to death. Although the speed of progression can vary, the average life expectancy following diagnosis is three to nine years.

In 2010, there were between 21 and 35 million people worldwide with Alzheimer's disease. With the aging of the population, in developed countries, Alzheimer's disease is one of the most financially costly diseases.

In the brains of patients suffering from Alzheimer's disease, Tau protein (a microtubule-associated protein that has a role in assembly and stabilization of microtubules) was found to be hyperphosphorylated, leading to aggregation of the protein and to a decrease in TAU binding to microtubules resulting in cell death. Phosphorylated TAU is also toxic to neuronal cells.

Other neurodegenerative diseases associated with the pathological aggregation of tau have been reported, and are collectively designated as "tauopathies".

Progress is being made in understanding the mechanisms underlying tauopathies such as Alzheimer's disease.

However, there remains a need in the art for efficient therapies and for biomarkers of the disease that would enable the detection of the disease at a very early stage.

SUMMARY OF THE INVENTION

The present invention relates to methods for the treatment and diagnosis of tauopathies such as Alzheimer's disease and traumatic brain injuries. More particularly, the present invention is based on the discovery that the splicing silencer, HNRNPC, plays a role in the aberrant splicing of the NXNL2 gene in the brain of patients suffering from Alzheimer's disease and that said aberrant splicing is associated with Alzheimer's disease.

In one aspect, the invention relates to an expression vector comprising a nucleic acid encoding heterogeneous nuclear ribonuclear protein C (HNRNPC).

The invention also relates to an expression vector comprising a nucleic acid encoding HNRNPC for use in a method for preventing and/or treating a tauopathy. The invention also relates to a pharmaceutical composition comprising an expression vector comprising a nucleic acid encoding HNRNPC.

In another aspect, the invention also relates to a method for detecting a risk of developing a tauopathy in a patient comprising the step of detecting the level of HNRNPC in a sample obtained from said patient.

DETAILED DESCRIPTION OF THE INVENTION

Expression Vectors, Pharmaceutical Composition and Therapeutic Methods of the Invention In one aspect, the invention relates to an expression vector comprising a nucleic acid encoding heterogeneous nuclear ribonuclear protein C (HNRNPC).

As used herein, the term "HNRNPC" or "heterogeneous nuclear ribonuclear protein C" refers to the RNA-binding protein encoded by the HNRNPC gene and identified by Stone et al. (JBC, 2002, 277, 15621-8). It encompasses both isoforms, HNRNPC1 and HNRNPC2, which differ by 13 amino acids.

The invention also relates to an expression vector comprising a nucleic acid encoding HNRNPC for use in a method for preventing and/or treating a tauopathy.

The invention also relates to a pharmaceutical composition comprising an expression vector comprising a nucleic acid encoding HNRNPC.

As used herein, the term "tauopathy" has its general meaning in the art. It refers to the class of neurodegenerative diseases associated with the pathological aggregation of tau protein in the brain. Tauopathies include, but are not limited to, Alzheimer's disease, traumatic brain injury, frontotemporal dementia, including the subtype of frontotemporal dementia and Parkinsonism linked to chromosome 17 (FTDP-17), progressive supranuclear palsy, corticobasal degeneration, Pick's disease, and agyrophilic grain disease.

In a particular embodiment, said tauopathy is selected from the group consisting of Alzheimer's disease and traumatic brain injury.

As used herein, the terms "prevention", "prevent", "preventing" refer to the fact of stopping/delaying the occurrence of tauopathy, reducing of the risk of tauopathy, or slowing down the development of said tauopathy. It can also refer to the prevention or slowing down of one or more symptoms of tauopathy (such as the pathological aggregation of tau protein).

As used herein, the terms "expression vector" refer to a nucleic acid molecule capable of directing the expression of a given nucleic acid sequence which is operatively linked to an expression control sequence or promoter. In particular, an expression vector according to the invention is a vector which enables the expression of a given nucleic acid sequence into the protein encoded by said nucleic acid sequence in a eukaryotic host cell. The promoter of said expression vector is typically a eukaryotic promoter.

The expression vector(s) of the present invention can be a plasmid or a viral vector. A plasmid is a circular double-stranded DNA loop that is capable of autonomous replication. A viral vector is a nucleic acid molecule which comprises viral sequences which can be packaged into viral particles. A variety of viral vectors are known in the art and may be adapted to the practice of this invention, including e.g., adenovirus, AAV, retrovirus, hybrid adeno-AAV, lentivirus and others. By carrying out routine experimentation, the skilled person in the art can chose from the variety of available vectors, those which are suitable for carrying out the method of the invention.

In a particular embodiment, the expression vector is an adeno-associated vector (AAV).

AAVs have been extensively described in the art as suitable vectors for gene delivery.

Indeed, AAVs are non-pathogenic and display a broad range of tissue specificity. Typically, AAVs according to the present invention are AAVs that are able to target the nucleic acid encoding HNRNPC to the brain.

Examples include, but are not limited to, AAV2, AAV2/8, AAV9, and AAV7m8.

The expression vector of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, sublingual, subcutaneous, intramuscular, intravenous, transdermal, local or mucosal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Sterile injectable solutions are prepared by incorporating the expression vector in the required amount in the appropriate solvent with one or several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1,000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

In a particular embodiment, the expression vector comprising a nucleic acid encoding HNRNPC is administered in combination with another active agent.

Typically, the expression vector can be administered in combination with an agent used to prevent tauopathy, such as anti-oxidant agent. Suitable anti-oxidant agents include, but are not limited to, natural antioxidants such as ascorbic acid (AA, E300) and tocopherols (E306), as well as synthetic antioxidants such as propyl gallate (PG, E310), tertiary butylhydroquinone (TBHQ), butylated hydroxyanisole (BHA, E320) and butylated hydroxytoluene (BHT, E321).

Typically, the agent used to prevent tauopathy can include, but is not limited to, cholinesterase inhibitors such as donepezil, galantamine and rivastigmine, and NMDA antagonists such as memantine.

Typically, the expression vector and the other active agent can be formulated separately. Alternatively, they can be formulated together in a pharmaceutical composition.

Diagnostic Methods of the Invention

In another aspect, the invention also relates to a method for detecting a risk of developing a tauopathy in a patient comprising the step of detecting the level of HNRNPC in a sample obtained from said patient.

As used herein, the term "patient" denotes a mammal, such as a rodent, a feline, a canine, a bovine, an equine, a sheep, a porcine and a primate. Preferably, a patient according to the invention is a human.

The biological sample suitable for carrying out the invention may be a body fluid, such as serum, plasma, blood or urine. It may also be a brain biopsy or a cerebrospinal fluid sample.

As used herein, the expression 'level of HNRNPC" has its general meaning in the art. It can refer to the enzymatic activity of HNRNPC, to the amount of HNRNPC protein or the amount of mRNA encoding HNRNPC in said biological sample. As used herein, a "decreased level of HNRNPC" is a level of HNRNPC which is lower than that observed in the general population. A level of HNRNPC is deemed to be lower than the general population, when it is lower than the normal by a factor 1.5, preferably 2, even more preferably 2, 3 . . . 10, or when it is not detectable.

In one embodiment, the level of HNRNPC can refer to level of HNRNPC enzymatic activity, i.e. to the capacity to regulate the splicing of the Nxnl2 gene.

In one aspect, the invention therefore relates to a method for detecting a predisposition to tauopathy in a patient comprising the step of detecting the level of HNRNPC enzymatic activity in a biological sample obtained from said patient.

Typically, the enzymatic activity of HNRNPC can be measured according to available enzymatic tests. Suitable enzymatic tests of HNRNPC levels can include, but are not limited to the measurement of the effect of HNRNPC on the splicing of the Nxnl2 gene products.

Indeed, the inventors have shown than the level of HNRNPC was correlated with the amount of aberrant alternatively spliced RdCVF2Lv2.

Without wishing to be bound by theory, it is thought that the introduction of a retrotransposon (AluSx) 3' to the NXNL2 gene in primate lineage results by exonisation in the production of aberrant alternatively spliced transcript NXNL2v2 with exon 2' instead of exon 2 that is translated as a protein RdCVF2Lv2 that is no longer able to interact with TAU contrarily to RdCVF2Lv1. This mechanism is called exonisation.

The inventors have shown that NXN2Lv2 is predominantly expressed in the brain of patients suffering from Alzheimer's disease as compared to age-matched controls.

Typically, one can measure the Nxnl2 v2/(v1+v2) expression ratio by carrying out the following test:

The total RNA from frozen brain specimens is purified by cesium chloride centrifugation (Delyfer et al., 2013). The quantification is done using Nanodrop 2000 (Thermo Scientific). The ratio of absorbance 260/280 nm is used to control protein contaminations. The integrity of the RNA is controlled using a Bioanalyzer (Bioanalyzer 2100, Agilent). The RNA is validated when the ratio of the two bands corresponding to the ribosomal RNA 28 Svedberg (S) and 18S is 2/1 and when the RNA integrity number (RIN) is close to 10. cDNA is produced using Superscript II reverse transcriptase kit (Life Technologie) using 2.5 µg of RNA. PCR is performed using specific primers. Data is normalized with the expression of the ribosomal RPS6 gene.

The sequences of the primers are as follows:

```
NXNL2v1 F:
                                           (SEQ ID No. 1)
AAGTGGTCTTCGTGTAGCC

NXNL2v1 R:
                                           (SEQ ID No. 2)
CCTCTTCCTCAGCTCATGCC

NXNL2v2 F:
                                           (SEQ ID No. 3)
GCCTGGCTGGCGCTG

NXNL2v2 R:
                                           (SEQ ID No. 4)
AGGCTAAGGCTAGTTCCTCA
```

```
-continued
RPS6 F:
                                           (SEQ ID No. 5)
TGCATTGTGGATGCAAATCT RPS6 R:
                                           (SEQ ID No. 6)
CTGGCGGACATCATCTTCTT
```

In a particular embodiment, the invention relates to a method for predicting a risk of developing a tauopathy in a patient comprising the step of detecting the Nxnl2 v2/(v1+v2) expression ratio in a biological sample obtained from said patient. Typically, an increase in said ratio compared to a standard ratio observed in a control population or in the general population is associated with an increased risk of developing a tauopathy.

Typically, the level of HNRNPC activity is deemed to be decreased if the level of HNRNPC activity measured the patient's sample is below a certain threshold.

In another embodiment, the level of HNRNPC is the level of the HNRNPC protein found in the biological sample.

In one aspect, the invention therefore relates to a method for detecting a predisposition to tauopathy in a patient comprising the step of detecting the level of the HNRNPC protein in a biological sample obtained from said patient.

In a particular embodiment, the methods of the invention comprise contacting the biological HNRNPC protein present in the biological sample. The binding partner may be an antibody that may be polyclonal or monoclonal, preferably monoclonal. In another embodiment, the binding partner may be an aptamer.

Polyclonal antibodies of the invention or a fragment thereof can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred.

Monoclonal antibodies of the invention or a fragment thereof can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985).

Alternatively, techniques described for the production of single chain antibodies (see e.g. U.S. Pat. No. 4,946,778) can be adapted to produce anti-HNRNPC single chain antibodies. Antibodies useful in practicing the present invention also include anti-HNRNPC fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to HNRNPC. For example, phage display of antibodies may be used. In such a method, single-chain Fv (scFv) or Fab fragments are expressed on the surface of a suitable bacteriophage, e. g., M13. Briefly, spleen cells of a suitable host, e. g., mouse, that has been immunized with a protein are removed. The coding regions of the VL and VH chains are obtained from those cells that are producing the desired antibody against the protein. These coding regions are then fused to a terminus of a phage sequence. Once the phage is inserted into a suitable carrier, e. g., bacteria, the phage displays the antibody fragment. Phage display of antibodies may also be provided by combinatorial methods known to those skilled in the art. Antibody fragments displayed by a phage may then be used as part of an immunoassay.

Antibodies against HNRNPC are available for example from name:

Anti-hnRNP C1+C2 antibody (4F4) Mouse monoclonal (Abcam ref: ab10294)

In another embodiment, the binding partner may be an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. 1997. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consist of conformationally constrained antibody variable regions displayed by a platform protein, such as *E. coli* Thioredoxin A, that are selected from combinatorial libraries by two hybrid methods (Colas et al., 1996).

The binding partners of the invention, such as antibodies or aptamers, may be labelled with a detectable molecule or substance, such as a fluorescent molecule, a radioactive molecule or any others labels known in the art. Labels are known in the art that generally provide (either directly or indirectly) a signal.

As used herein, the term "labelled", with regard to the antibody, is intended to encompass direct labelling of the antibody or aptamer by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody or aptamer, as well as indirect labelling of the probe or antibody by reactivity with a detectable substance. An antibody or aptamer of the invention may be labelled with a radioactive molecule by any method known in the art. For example radioactive molecules include but are not limited radioactive atom for scintigraphic studies such as I123, I124, In111, Re186, Re188.

The aforementioned assays generally involve the binding of the binding partner (ie. antibody or aptamer) to a solid support. Solid supports which can be used in the practice of the invention include substrates such as nitrocellulose (e. g., in membrane or microtiter well form); polyvinylchloride (e. g., sheets or microtiter wells); polystyrene latex (e.g., beads or microtiter plates); polyvinylidine fluoride; diazotized paper; nylon membranes; activated beads, magnetically responsive beads, and the like.

The level of the HNRNPC protein may be measured by using standard immunodiagnostic techniques, including immunoassays such as competition, direct reaction, or sandwich type assays. Such assays include, but are not limited to, agglutination tests; enzyme-labelled and mediated immunoassays, such as ELISAs; biotin/avidin type assays; radioimmunoassays; immunoelectrophoresis; immunoprecipitation.

More particularly, an ELISA method can be used, wherein the wells of a microtiter plate are coated with a set of antibodies against HNRNPC. The biological sample is then added to the coated wells. After a period of incubation sufficient to allow the formation of antibody-antigen complexes, the plate(s) can be washed to remove unbound moieties and a detectably labelled secondary binding molecule added. The secondary binding molecule is allowed to react with any captured sample marker protein, the plate washed and the presence of the secondary binding molecule detected using methods well known in the art.

In a particular embodiment, the method for detecting a risk of developing a tauopathy according to the present invention comprises the step of detecting a fragment of HNRNPC by semi-quantitative Western blot in a cerebrospinal fluid sample obtained from said patient.

Similar approaches have been successfully carried out for other biomarkers of neurodegenerative disease (see Huhmer et al., 2006).

In an alternative embodiment, the level of HNRNPC can be measured by measuring the amount of messenger RNA (mRNA) encoding HNRNPC.

In one aspect, the invention therefore relates to a method for detecting a risk of developing a tauopathy in a patient comprising the step of detecting the level of mRNA encoding HNRNPC in a biological sample obtained from said patient.

Typically, said method can comprise a step of isolating total RNA or total mRNA from said biological sample, prior to the detection of the level of mRNA encoding HNRNPC.

The skilled person in the art knows how to carry out such isolating steps using standard procedures.

Methods for detecting the presence of mRNA are well known in the art. For example the nucleic acid contained in the samples is first extracted according to standard methods, for example using lytic enzymes or chemical solutions or extracted by nucleic-acid-binding resins following the manufacturer's instructions. The extracted mRNA is then detected by hybridization (e. g., Northern blot analysis) and/or amplification (e.g., RT-PCR). In a preferred embodiment, the expression of the HNRNPC gene or is detected by RT-PCR, preferably quantitative or semi-quantitative RT-PCR, even more preferably real-time quantitative or semi-quantitative RT-PCR.

Other methods of amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to the mRNA of interest herein find utility as hybridization probes or amplification primers. It is understood that such nucleic acids need not be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e. g. avidin/biotin).

Probes typically comprise single-stranded nucleic acids of between 10 to 1000 nucleotides in length, for instance of between 10 and 800, more preferably of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate).

The nucleic acid primers or probes used in the above amplification and detection method may be assembled as a kit. Such a kit includes consensus primers and molecular probes. A preferred kit also includes the components necessary to determine if amplification has occurred. The kit may also include, for example, PCR buffers and enzymes; positive control sequences, reaction control primers; and instructions for amplifying and detecting the specific sequences.

In a preferred embodiment, said kit comprises oligonucleotides for determining the level of HNRNPC mRNA by quantitative PCR. Typically, said kit can comprise oligonucleotides specific for the HNRNPC mRNA and internal normalization oligonucleotides (housekeeping genes).

In a further embodiment, the level of HNRNPC can be assayed indirectly by genotyping the HNRNPC gene.

In one aspect, the invention therefore relates to a method for detecting a risk of developing a tauopathy in a patient comprising the step of detecting the level of HNRNPC in a biological sample obtained from said patient, wherein said level of HNRNPC is assayed indirectly by genotyping the HNRNPC gene.

Typically, said method can comprise a step of isolating DNA from said biological sample, prior to the detection of mutations in the gene encoding HNRNPC.

The skilled person in the art knows how to carry out such isolating steps using standard procedures.

A decreased expression of the HNRNPC gene resulting in lower levels of HNRNPC-encoding mRNA and/or lower levels of HNRNPC protein can be due to mutations in the HNRNPC promoter or in the HNRNPC coding sequence. Alternatively, certain decreased activity of HNRNPC can be due to mutations in the coding sequence which do not influence the expression levels.

As used herein, the expression "risk of developing a tauopathy" refers to a patient's susceptibility or proneness to develop a tauopathy of any type.

Said risk of developing a tauopathy may be purely hereditary predisposition (inherited mutation for example) or acquired (spontaneous mutations, epigenetic regulations etc.). It has been shown that certain environmental conditions (such as exposure to oxidative stress) increase the risk for a patient of developing a tauopoathy. A "risk of developing a tauopathy" can be defined as an increased risk of developing a tauopathy, when compared to the general population.

The invention will be further described by the following examples and figures, which are not intended to limit the scope of the protection defined by the claims.

FIGURE LEGENDS

FIG. 1: Decreased expression of the splicing inhibitor protein HNRNPC in the brain of Alzheimer patients.

Western blot of HNRNPC1/C2 on brain protein extracts obtained from patients suffering from Alzheimer's disease (lanes 13 to 22) and age-matched controls (lanes 1 to 12).

The two bands correspond to the two isoforms C1 and C2 of the HNRNPC protein.

Figure 2:
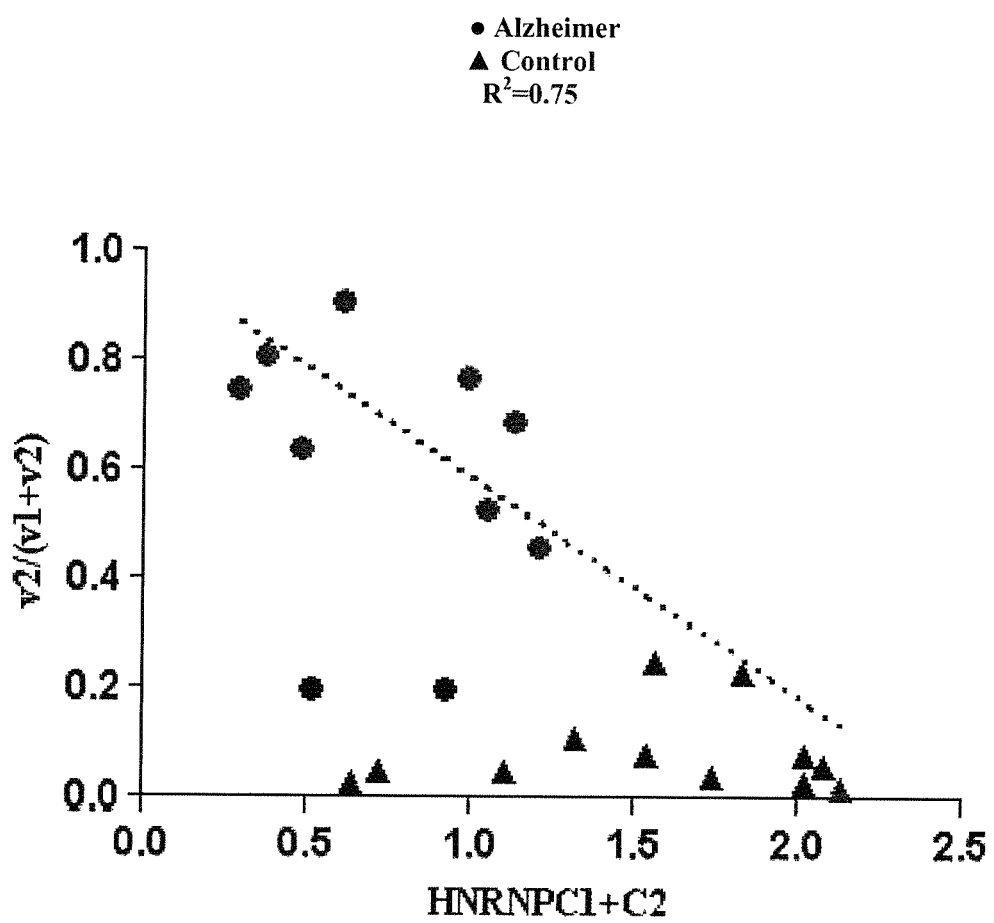

FIG. 2: Correlation between the expression of HNRPNC and that of NXNL2v2.

The ratio of expression v1/(v1+v2) transcripts of the NXNL2 gene is correlated to the level of expression of HNRNPC in brain samples obtained from patients suffering from Alzheimer's disease. The dashed line represents the regression curve ($R2=0,7513$) based on the values obtained for Alzheimer patients, with the exclusion of 2 patients who presented a different profile (see the 2 circles with a v2/(v1+v2) ratio around 0.2).

The expression levels of isoforms NXNL2v1 and NXNL2v2 were assessed by quantitative RT-PCR.

EXAMPLES

The inventors have demonstrated the involvement of the Nxnl2 gene in Alzheimer's disease, based the abnormal behavior of the Nxnl2−/− mouse. The aged Nxnl2−/− mice have visual and olfactory deficit (Jaillard et al., 2012), but interestingly, these mice have cognitive deficits that can be scored at 2 months of age before the animals show visual and olfactory dysfunction (Jaillard et al., Manuscript in preparation). These phenotypes were not observed in the Nxnl1−/− mouse in agreement with its expression restricted to the retina. The Nxnl2−/− mouse is hyperactive as demonstrated by the open field test, and has increased anxiety as shown by the elevated plus maze test. This mouse has additional deficits in working memory seen in the Y maze test, contextual memory deficit as seen in fear conditioning, and in spatial memory in the Morris water maze test. However, this mouse has no motor deficit as judged by the rotarod test. The Morris water maze is a standard method for evaluation of spatial learning and memory ability, and reflects cognitive defects directly associated with dysfunction of the hippocampus.

As for RdCVFL, one of the products of the Nxnl1 gene, TAU interacts with the thioredoxin-like protein RdCVF2L, and not with the trophic factor RdCVF2. RdCVF2L inhibits TAU phosphorylation. By 18 months of age, astrogliosis can be observed in the hippocampus of the Nxnl2−/− brain. At the same age, the analysis of whole brain extracts shows presence of aggregates of TAU as seen by filter binding assay, as well as oligomeric forms of TAU. While the expression of TAU is not modified by the inactivation of the Nxnl2 gene, TAU is phosphorylated in the brain of the Nxnl2−/− mouse as shown using two distinct anti-phospho-TAU antibodies, AT8 and AT100. Interestingly, the expression of NXNL2 is reduced by 48% in the frontal cortex of patients deceased from Alzheimer's disease as compared to age-matched controls.

The expression of the NXNL2 gene in brain specimens of from patients deceased from Alzheimer's disease was investigated and compared to control specimens. The inventors observed that the NXNL2 gene in human brain tissues expressed an additional and unsuspected splicing isoform. Based on these observations we studied splicing regulation of the NXNL2 gene. The introduction of a retrotransposon (AluSx) in reverse orientation, 3' to the NXNL2 gene in primate lineage results in exonisation in the production of aberrant alternatively spliced transcript NXNL2v2 with exon 2' coming from the AluSx sequence instead of the normal exon 2. This transcript is translated as a protein RdCVF2Lv2 that is no longer able to interact with TAU contrarily to RdCVF2Lv1. Splice site selection occurs through the coordinated recognition of multiple cis-elements: the branch point, the 5' splice site (donor site), the polypyrimidine tract (PPT), the 3' splice site (acceptor site), and a variety of auxiliary elements (Hertel, 2014). NXNL2v2 expression pattern results from the very efficient PPT rich in thymidines, provided by the AluSx sequence in reverse orientation. This mechanism is called exonisation and is known to be regulated by the splicing inhibitor factor HNRNPC (Zarnack et al., 2013). NXN2Lv2 is predominantly expressed in the brain of Alzheimer's disease patients as compared to age-matched and examined control brain specimens. The inventors observed a reduction of the expression of HNRPPC in the cortex of Alzheimer patients that is correlated with the ratio of expression (v2/v1+v2). They confirmed the reduction of the expression of HNRNPC by immunohistochemistry. Interestingly, in HEK293 cells the oxidative agent diamide increases the ratio of expression (v2/v1+v2). Furthermore, the inventors found that diamide treatment results in the nuclear exclusion of HNRNPC. 2D gel electrophoresis showed that this agent induces a post-translational modification of the HNRNPC protein, most likely by an inhibitory phosphorylation (Stone and Collins, 2002). The increased exonisation of the NXNL2 genes by oxidative stress raises the ratio (v2/v1+v2) and consequently the relative expression of the RdCVF2Lv2 that is no longer able to interact with TAU (Camara et al., Manuscript in preparation). This is a clear demonstration of an epigenetic mechanism of Alzheimer's disease progression, where the reduction of HNRNPC level will alter the expression of many genes with an Alu retrotransposon.

In conclusion, the inventors have shown that the splicing inhibitor HNRNPC is down-regulated in the brain tissue of patients suffering from Alzheimer's disease, compared to age-matched control patients (FIG. 1).

They have also demonstrated, using transient transfection of siRNA directed against HNRNPC, that the diminution of the expression of HNRNPC induces an increase of NXNLv2 (data not shown).

The ratio of expression v1/(v1+v2) is correlated to the level of expression of HNRNPC (FIG. 2).

REFERENCES

Throughout this application, various references describe the state of the art to which this invention pertains. The disclosures of these references are hereby incorporated by reference into the present disclosure.

Camara, H., Argentini, M., Clerin, E., Blond, F., Ferracane, V., Milllet-Puel, G., Aït-Ali, N., Kole, C., Sahel, J. A., and Léveillard, T. (Manuscript in preparation). Aberrant exonisation on the Nucleoredoxin-like 2 gene, a epigenetic mechanism in Alzheimer's disease Delyfer, M. N., Ait-Ali, N., Camara, H., Clerin, E., Korobelnik, J. F., Sahel, J. A., and Leveillard, T. (2013). Transcriptomic Analysis of Human Retinal Surgical Specimens Using jouRNA1. Journal of visualized experiments: JoVE.

Hertel, K. J. (2014). Spliceosomal pre-mRNA splicing methods and protocols (New York u.a.: Humana Press).

Huhmer et al. (2006). Protein analysis in human cerebrospinal fluid: Physiological aspects, current progress and future challenges. Disease markers 22, 3-26.

Jaillard, C., Mouret, A., Niepon, M. L., Clerin, E., Yang, Y., Lee-Rivera, I., Ait-Ali, N., Millet-Puel, G., Cronin, T., Sedmak, T., et al. (2012). Nxnl2 splicing results in dual functions in neuronal cell survival and maintenance of cell integrity. Human molecular genetics 21, 2298-2311.

Jaillard, C., Ouechtati, F., Clérin, E., Niepon, M. L., Meziane, H., Fridlich, R., Lambert, J. C., Amouyel, P., Sahel, J. A., and Léveillard, T. (Manuscript in preparation). The inactivation of the Nxnl2 gene in the mouse reveals its implication in Alzheimer's disease.

Liu, N., Dai, Q., Zheng, G., He, C., Parisien, M., and Pan, T. (2015). N(6)-methyladenosine-dependent RNA structural switches regulate RNA-protein interactions. Nature 518, 560-564.

Stone, J. R., and Collins, T. (2002). Rapid phosphorylation of heterogeneous nuclear ribonucleoprotein C1/C2 in response to physiologic levels of hydrogen peroxide in human endothelial cells. The Journal of biological chemistry 277, 15621-15628.

Zarnack, K., Konig, J., Tajnik, M., Martincorena, I., Eustermann, S., Stevant, I., Reyes, A., Anders, S., Luscombe, N. M., and Ule, J. (2013). Direct competition between hnRNP C and U2AF65 protects the transcriptome from the exonization of Alu elements. Cell 152, 453-466.

The invention claimed is:

1. A method of decreasing a level of TAU phosphorylation in a subject in need thereof, comprising
    administering to the cortex of the brain of said subject an expression vector encoding heterogeneous nuclear ribonuclear protein C (HNRNPC), in a sufficient amount to increase the level of HNRNPC in said cortex, wherein said increase in the level of HNRNPC decreases levels of TAU phosphorylation.

2. The method of claim 1, wherein the subject has a low level of HNRNPC in the cortex.

3. The method according to claim 1, wherein said subject has Alzheimer's disease or a traumatic brain injury.

4. The method of claim 1, further comprising a step of detecting the level of HNRNPC in a biological sample obtained from said subject, and wherein the step of administering is performed when the level is below a preselected level.

5. The method according to claim 4, wherein said biological sample is a brain sample or a cerebrospinal fluid sample.

6. The method according to claim 4, wherein said level of HNRNPC is the level of the HNRNPC protein.

7. The method according to claim 4, wherein said level of HNRNPC is the level of mRNA encoding HNRNPC.

8. The method according to claim 4, wherein said level of HNRNPC is assayed indirectly by genotyping the HNRNPC gene.

* * * * *

SEQUENCE LISTING

```
<160> NUMBER OF SEQ ID NOS: 6

<210> SEQ ID NO 1
<211> LENGTH: 19
<212> TYPE: DNA
<213> ORGANISM: Homo sapiens

<400> SEQUENCE: 1
aagtggtctt cgtgtagcc                                           19

<210> SEQ ID NO 2
<211> LENGTH: 20
<212> TYPE: DNA
<213> ORGANISM: Homo sapiens

<400> SEQUENCE: 2
cctcttcctc agctcatgcc                                          20

<210> SEQ ID NO 3
<211> LENGTH: 15
<212> TYPE: DNA
<213> ORGANISM: Homo sapiens

<400> SEQUENCE: 3
```

```
gcctggctgg cgctg                                            15

<210> SEQ ID NO 4
<211> LENGTH: 20
<212> TYPE: DNA
<213> ORGANISM: Homo sapiens

<400> SEQUENCE: 4
aggctaaggc tagttcctca                                       20

<210> SEQ ID NO 5
<211> LENGTH: 20
<212> TYPE: DNA
<213> ORGANISM: Homo sapiens

<400> SEQUENCE: 5
tgcattgtgg atgcaaatct                                       20

<210> SEQ ID NO 6
<211> LENGTH: 20
<212> TYPE: DNA
<213> ORGANISM: Homo sapiens

<400> SEQUENCE: 6
ctggcggaca tcatcttctt                                       20
```